United States Patent
Ito

(10) Patent No.: US 9,012,233 B2
(45) Date of Patent: Apr. 21, 2015

(54) WATER ABSORBING MATERIAL

(75) Inventor: Hiroshi Ito, Minato-ku (JP)

(73) Assignee: Daiki Co., Ltd., Tokyo (JP)

( * ) Notice: Subject to any disclaimer, the term of this patent is extended or adjusted under 35 U.S.C. 154(b) by 331 days.

(21) Appl. No.: 13/487,916

(22) Filed: Jun. 4, 2012

(65) Prior Publication Data
US 2012/0288955 A1 Nov. 15, 2012

Related U.S. Application Data

(63) Continuation of application No. PCT/JP2011/054534, filed on Feb. 28, 2011.

(51) Int. Cl.
| | |
|---|---|
| G01N 21/00 | (2006.01) |
| A61L 15/60 | (2006.01) |
| A01K 1/015 | (2006.01) |
| A61F 13/42 | (2006.01) |

(52) U.S. Cl.
CPC ............... *A61L 15/60* (2013.01); *A01K 1/0152* (2013.01); *A61F 13/42* (2013.01)

(58) Field of Classification Search
None
See application file for complete search history.

(56) References Cited

U.S. PATENT DOCUMENTS

| | | | |
|---|---|---|---|
| 6,745,720 B2* | 6/2004 | Rasner et al. | 119/172 |
| 2008/0295778 A1* | 12/2008 | Pero et al. | 119/173 |

FOREIGN PATENT DOCUMENTS

JP    A-2000-333547    12/2000

* cited by examiner

*Primary Examiner* — Robert Xu
(74) *Attorney, Agent, or Firm* — Oliff PLC

(57) ABSTRACT

Provided is a water absorbing material having a granular core portion and a coating layer portion coating the granular core portion, which enables a test result after use to be clearly determined by developing vivid and uniform color. In the water absorbing material, the coating layer portion is composed of 90 wt % to 96 wt % of a substrate and 10 wt % to 4 wt % of an excretion test material, the excretion test material contains a porous adsorbent having an adsorbance of 20 wt % or greater and including micropores, and an excretion test indicator adsorbed on the micropores of the porous adsorbent, and the excretion test indicator is added in an amount more than 0.1 wt % and not more than 1.0 wt % relative to the total amount of the coating layer portion.

6 Claims, 1 Drawing Sheet

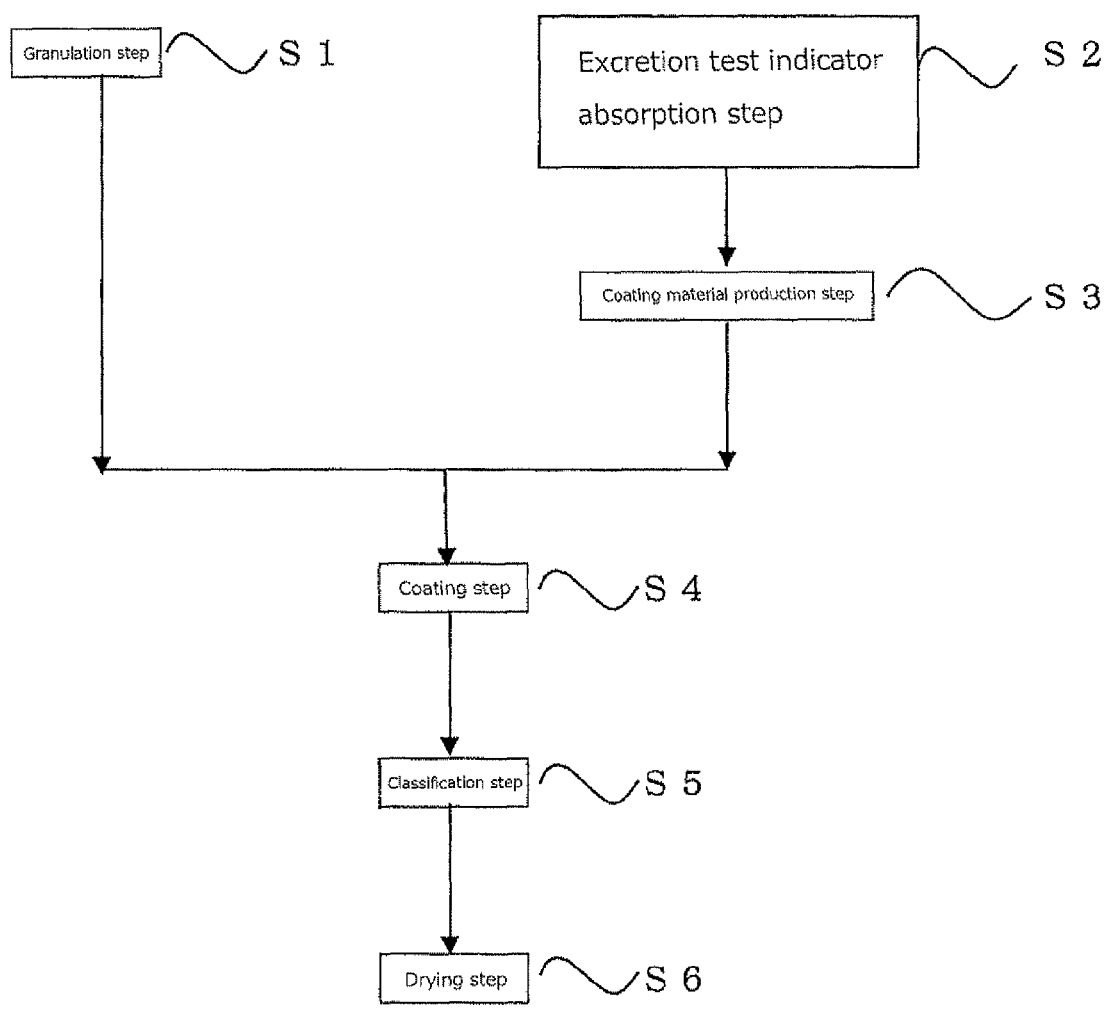

WATER ABSORBING MATERIAL

TECHNICAL FIELD

The present invention relates to a granular water absorbing material having a function to test urine in fluids such as excretions of humans or animals (hereinafter simply referred to as a "water absorbing material").

BACKGROUND ART

Recently, the number of people who like pets and like animals has been increasing, and many pet owners pay attention to pet health just like human health. There is a limit to checking a change of the health condition of a pet by observation of pet's appearance, and therefore, in order to readily discover such a change of the condition at an early stage, a water absorbing material (excretion treating material) formed in a granular shape and containing a pH indicator has been used (Patent Literature 1).

CITATION LIST

Patent Literature

[PLT 1]
JP 2000-333547A

SUMMARY OF INVENTION

Technical Problem

However, this water absorbing material is produced by dissolving an ink composition containing a pH indicator in water and spraying the dilution onto the surface layer of a water absorbing material that has been formed into granules. Therefore, there has been a problem in that it is difficult in some cases to uniformly spray the pH indicator onto the surface layer and to achieve vivid and uniform color. Also, in recent years, even a water absorbing material containing an indicator that has a function to test urine is required to have an agreeable appearance (i.e., to be formed so as to have an appearance that matches a place where the material is used by, for example, coloring the material), but there has been a problem in that in the case where a generally used pigment is blended and coloring or the like is performed, such a pigment inhibits a test. In addition, water absorbing materials have to be disposed of after use, and an indicator that has a function to test urine is expensive, and thus it has been desired that water absorbing materials are produced as inexpensively as possible.

The present invention was accomplished to solve the foregoing problems, and an object thereof is to provide a water absorbing material that enables a test result after use to be clearly determined by developing vivid and uniform color, that has an excellent appearance, and that can be produced inexpensively and easily.

Solution to Problem

To solve the foregoing problem, the water absorbing material of the present invention is a water absorbing material including a granular core portion and a coating layer portion coating the granular core portion, the coating layer portion is composed of 90 wt % to 96 wt % of a substrate and 10 wt % to 4 wt % of an excretion test material, the excretion test material contains a porous adsorbent having an absorbance of 20 wt % or greater (more preferably 25 wt % or greater) and including micropores, and an excretion test indicator (hereinafter referred to as a "test indicator") adsorbed on the micropores of the porous adsorbent, and the test indicator is added in an amount more than 0.10 wt % and not more than 1.0 wt % (more preferably 0.15 wt % to 0.50 wt %) relative to the total amount of the coating layer portion.

Here, it is necessary to allow the aforementioned test indicator to be adsorbed on the porous adsorbent, and therefore, although the adsorption method is not particularly specified, it is preferable that the test indicator is fixed while being in a solvent-dissolved state (in particular, fixed as an ink composition).

Also, the test indicator is a reagent of any type that changes its color upon reaction with excretion such as urine, and it is thus possible to perceive a change of health condition or the like. Urinary pH value detection indicators for detecting a urinary pH value (hereinafter referred to as "urinary pH value test indicators"), urinary glucose detection indicators, urinary protein detection indicators, urinary occult blood detection indicators, urinary urobilinogen detection indicators, and like known indicators are usable.

Regarding the water absorbing material of the present invention, a test indicator is not directly added, but the test indicator is adsorbed on a porous adsorbent. Since the test indicator is evenly adsorbed in a large number of pores present in the porous adsorbent, it is possible to uniformly retain the test indicator in an amount that enables a color change or a lightness change (hereinafter collectively referred to as a "color change") to be clearly identified without carrying out a special treatment.

Since the test indicator is blended in the coating layer portion, the coating layer portion promptly undergoes a color change as the test indicator is brought into contact, and it is thereby possible to readily determine a test result in a short period of time. Moreover, since the test indicator is added in an amount more than 0.1 wt % and not more than 1.0 wt % relative to the total amount of the coating layer portion, it is possible to achieve color development so as to attain specific lightness and chroma before use, thus making it possible to retain agreeable appearance.

Advantageous Effects of Invention

According to the present invention, it is possible to provide a water absorbing material that enables a test result after use to be clearly determined by developing vivid and uniform color, that has an excellent appearance, and that can inexpensively and easily be produced.

BRIEF DESCRIPTION OF DRAWING

[FIG. 1]
FIG. 1 is a flowchart showing a method for producing a water absorbing material of the present invention.

DESCRIPTION OF EMBODIMENTS

One aspect (hereinafter referred to as an "embodiment") of carrying out the present invention will now be described in detail in reference to the drawing, using as an example of a granular multilayer water absorbing material for treating excretion (urine treating material) for a pet such as a cat or a dog.

The test indicator is described using a urinary pH value test indicator as an example.

[Water Absorbing Material]

The water absorbing material of the present invention (hereinafter referred to as the "present water absorbing material") has a multi-layer structure composed of a granular core portion for absorbing moisture from outside and a coating layer portion having a specific thickness and coating the surface of the granular core portion.

(1) Granular Core Portion

It is sufficient that the granular core portion is formed in a pellet shape, and the granular core portion does not have to be, for example, perfectly spherical. The shape thereof is not limited to columnar (elongated), flat, or the like.

The granular core portion has water absorbability or water retainability, and the materials and other features thereof are not limited as long as a substance that inhibits testing when carrying out testing of excretion (for example, in the case where a change of the pH value of excretion is to be observed, a substance that prevents pH change) is not contained.

Usable examples include virgin pulp, toilet paper wastes, tissue paper wastes, facial paper wastes, cleaning paper wastes, cellulose wadding wastes, paper towel wastes, non-woven-fabric wastes, and like organic wastes that do not inhibit testing of a pH value.

Also, bentonite, zeolite, titanium oxide, and such inorganic materials as well as other materials can be used for the granular core portion.

It is possible to blend a deodorizing material, an odor eliminating material, a substance having bactericidal properties, a coloring substance, and a substance that can provide other effects without inhibiting water absorbability.

(2) Coating Layer Portion

The primary purpose of providing the coating layer portion is to demonstrate an action of causing grains of the water absorbing material wet with excretion such as urine when used to adhere to each other so as to form an aggregate. In the case where the granular core portion is originally colored, the second purpose of providing the coating layer portion is to hide the color of the granular core portion before use by coating the periphery thereof.

The coating layer portion is composed of a substrate and an excretion test material.

<Substrate>

The role for achieving the purposes of the coating layer portion is played by the substrate. As for the materials thereof, it is preferable to use, for example, an absorbent material, a water soluble material having adhesion (hereinafter referred to as a "water soluble adhesive material"), a mixture of both materials, or a mixture of paper dust.

As these substances, known substances that do not inhibit testing when carrying out testing of excretion are usable. Usable examples of the absorbent material include CMC (carboxymethyl cellulose), polyvinyl alcohol (PVA), starch (T-pregelatinized starch, dextrin, wheat starch, potato starch), and like materials having water absorbability.

Examples of the water soluble adhesive material include starch adhesives, sodium polyacrylate, and like highly absorbent materials. Usable as a starch adhesive that functions as such an adhesive are starches such as potato starch, wheat starch, sweet potato starch, corn starch (that does not inhibit testing), tapioca starch, rice starch, dextrin, and gelatinized (a) forms of these starches, acrylamide, PVA, carboxymethylcellulose, and sodium alginate, and two or more of these materials are usable in combination.

Examples of paper dust include virgin pulp, toilet paper, toilet paper wastes, tissue paper, tissue paper wastes, cleaning paper, cleaning paper wastes, cellulose wadding, cellulose wadding wastes, paper towel, paper towel wastes, cotton-like pulp, cotton-like pulp wastes, paper dust generated in non-woven fabric production, and a mixture of pulverized products of two or more of these materials. All these materials are used after being pulverized into particulates having a particle size of 0.5 millimeters or less, and preferably 0.3 millimeters or less.

<Excretion Test Material>

The excretion test material is a material in which an ink composition containing a test indicator (hereinafter referred to as a "test indicator-containing ink composition") is adsorbed on a porous adsorbent.

(Test Indicator-containing Ink Composition)

The test indicator-containing ink composition is a composition in which a test indicator is fixed to an ink composition.

Test Indicator

In the measuring of the pH value of excretion, the pH value of urine is detected and, for example, persistent aciduria or alkaluria is detected, and a purpose of the measurement is to judge necessity of treatment of lithiasis or other diseases. Since the pH value of urine of a healthy carnivore such as a dog or a cat is 4.3 to 7.0, a pH value less than 4.3 when diseased or a pH value greater than 7.0 when diseased can be identified by color change relative to a pH value of 4.3 to 7.0 when normal (when healthy), or that is, use of a urinary pH value test indicator that undergoes color change at the threshold pH value of 4.3 or 7.0 allows identification thereof.

Also, since the pH value of human urine is 4.6 to 7.5 in a healthy person who eats ordinary meals, a pH value less than 4.6 when diseased or a pH value greater than 7.5 when diseased can be identified by color change, or that is, use of a urinary pH value test indicator that undergoes color change at the threshold pH value of 4.6 or 7.5 allows identification thereof.

Examples of urinary pH value test indicators having a color change range at such a pH value, i.e., within the pH range of 4.1 to 7.7 include thymol blue, phenolphthalein, tropaeolin OOO, cresol red, phenol red, neutral red, bromothymol blue, bromocresol purple, bromophenol red, p-nitrophenol, methyl red, bromocresol green, tetrabromophenol blue, chlorophenol red, methyl orange, ethyl orange, bromophenol blue, brilliant yellow, congo red, bromocresol blue, and the like, and therefore, depending on the purpose of detection, the aforementioned indicators can be used singly or as a combination of two or more indicators.

Note that mixing two or more suitable indicators makes it possible to set a desired color change range and to attain desired color development, and is thus preferable. Also, a universal indicator with which a pH value can be measured throughout the entire pH range can also be used.

For instance, in the case where the color change threshold is at a pH value of 4.3, bromphenol blue or methyl orange and bromocresol green dissolved in ethanol can be used, and in the case where the color change threshold is at a pH value of 7.0, bromthymol blue can be used.

Ink Composition

The test indicator containing ink composition is a composition in which a test indicator and a binder are fixed to a known ink composition. In the present embodiment, it can be prepared by, for example, dispersing or dissolving the urinary pH value test indicator and at least one of resins such as cellulose and derivatives of the cellulose (hereinafter collectively referred to as "resin") in an organic solvent. Specifically, resin is added to the urinary pH test indicator and the mixture is dispersed or dissolved in an organic solvent, e.g., an alcohol such as methanol or ethanol, an aromatic hydrocarbon such as toluene, an ester such as propyl acetate, or the like to form the test indicator-containing ink composition.

For resin, preferable are cellose, methylcellulose, ethylcellulose, hydroxypropylcellulose, hydroxypropylmethylcellulose, carboxymethylcellulose, and the like in terms of wettability and ease of visual determination. In this case, as a solvent, it is preferable to select a solvent that can stably dissolve or disperse the test indicator and a resin that serves as the binder.

As binders, there are water soluble polymer compounds that do not affect testing of excretion, that do not prevent color production of the test indicator, and that stabilize the produced color (natural hydrophilic polymer compounds, semisynthetic hydrophilic polymer compounds) as well as water insoluble polymer compounds that do not affect testing of excretion, that do not prevent color production of the test indicator, and that function to form a film. It is preferable to use both types of binder in combination.

Usable examples of the natural hydrophilic polymer compounds include sweet potato starch, potato starch, arum root powder, funori seeweed, sodium alginate, *Abelmoschu manihot*, tongaro gum, gum arabic, dextran, levan, nikawa glue, gelatin, casein, collagen, and the like.

Usable examples of the semisynthetic hydrophilic polymer compounds include methylcellulose, hydroxypropylcellulose, hydroxyethylcellulose, carboxymethylcellulose, and like cellulosic derivatives, dialdehyde starch derivatives, and the like.

Usable examples of the water insoluble polymer compounds that function to form a film include nitrocellulose, cellulose acetate, ethylcellulose, cellulose acetate butyrate, and like cellulosic resins as well as polyester resin, alkyd resin, polyurethane resin, epoxy resin, acrylic resin, vinyl chloride resin, vinyl chloride copolymer resin, polyvinyl butyral, polyvinyl acetate emulsion, vinyl acetate copolymer (such as vinyl acetate-acrylic ester) emulsion, acrylic ester copolymer emulsion, epoxy resin emulsion, synthetic rubber latex, and the like. Among these polymer compounds that function to form a film, urethane resin and polyvinyl butyral, in particular, do not adversely affect the color change of the test indicator or the measurement of a pH value, and are thus preferable.

Moreover, known additives such as binders, stabilizers, or surfactants that enable formation of a uniform reagent layer (nonionic surfactants, anionic surfactants, cationic surfactants, amphionic surfactants, polyethylene glycol, or the like) can be added to the test indicator-containing ink composition.

Generally, the components of the test indicator-containing ink composition and their content ratios are as follows: test indicator and binder 1 wt % to 10 wt %, cellulose and the like 1 wt % to 15 wt %, adhesive 10 wt % or less, with the remainder being composed of a solvent.

(Porous Adsorbent)

For the porous adsorbent, it is necessary to use an adsorbent including a large number of micropores (fine apertures) and having a large surface area and an adsorbance of 20 wt % or greater (more preferably 25 wt % or greater). It is possible to use known substances such as silica gel (so-called type A silica gel and type B silica gel) (silicon dioxide) and zeolite (aluminosilicate). In particular, type B silica gel (an average absorbing surface area of about 450 ($m^2/g$), an average micropore size of about 60 Å, a micropore volume of about 0.75 (ml/g)) has a larger micropore size and a larger micropore volume than type A silica gel (an average absorbing surface area of about 700 ($m^2/g$), an average micropore size of about 24 Å, a micropore volume of about 0.46 (ml/g)), and thus demonstrates a high level of adsorbability when adsorbing the test indicator-containing ink composition and is thus highly preferable.

Also, a penetrating agent or a swelling agent can be added to the coating layer portion. As the penetrating agent, known substances such as various surfactants can be used, and as the swelling agent, known substances such as cellulose-based swelling agents can be used.

<Other Additives>

In the case where particles of a ground product of nonwoven fabric are used in the water absorbing material of the present invention, the particles of the ground product adhere to each other and form an aggregate when excretion is discharged. Therefore, in order to make it easy to handle the excretion treating material after discharging, an adhesive that is a starch adhesive having adhesion and not affecting testing of urine is added. As such an adhesive, water soluble polymer compounds such as natural hydrophilic polymer compounds and semisynthetic hydrophilic polymer compounds for use as a binder in the test indicator-containing ink composition can be used.

Also, a penetrating agent or a swelling agent can be added to the coating layer portion. As the penetrating agent, known substances such as various surfactants can be used, and as the swelling agent, known substances such as cellulose-based swelling agents can be used.

Proportions of Respective Materials

It is most preferable that the present water absorbing material has proportions of its components of 80 wt % to 87 wt % of the granular core portion and 20 wt % to 13 wt % of the coating layer portion in connection with the size of the granular core portion, the thickness of the coating layer portion, and the proportion of water soluble dye added, which will be described below.

The coating layer portion is composed of 90 wt % to 96 wt % of a substrate and 10 wt % to 4 wt % of an excretion test material.

It is necessary that the test indicator in the excretion test material is added in an amount more than 0.1 wt % and not more than 1.0 wt % (more preferably 0.15 wt % to 0.50 wt %) relative to the total amount of the coating layer portion. Therefore, when the test indicator is fixed to an ink composition, it is necessary to adjust the amounts of the solvent and other components such that the amount of the test indicator is within the aforementioned range and to determine the amount of the porous adsorbent according to the type thereof.

In order to maintain the agreeable appearance of the water absorbing material before use, it is necessary to have the water absorbing material develop, in advance, color having specific lightness and chroma (in particular, lightness is important). When the amount of the test indicator added to the foregoing excretion testing material is excessively small, no color development is attained before use. Meanwhile, the amount of the test indicator that can be adsorbed is determined according to the porosity of the porous adsorbent, and thus even when the test indicator is added in an amount that is more than necessary, the extent (lightness) of color development will not change before and after use. Accordingly, the inventors conducted extensive experiments and found the aforementioned suitable amount.

[Production Method]

Next, the method for producing a water absorbing material of the present invention is described in reference to FIG. 1.

The method for producing an excretion treating material of the present invention includes a granulation step (S1), an excretion test indicator adsorption step (S2), a coating material production step (S3), a coating step (S4), a classification step (S5), and a drying step (S6).

(1) Granulation Step (S1)

This step is for forming a granular core portion.

In this step, components such as pulp wastes are pulverized with a crusher so as to have a specific size, and the pulverized components are placed in a mixer and mixed such that specific proportions are attained. Then, water is added to increase the moisture content, and then the mixed components are subjected to extrusion granulation. In this manner, a granular core portion forming operation is performed.

The coating material adheres to the periphery of the granular core portion due to moisture present in the granular core portion. Therefore, when moisture is contained in an amount less than the lower limit of the moisture content of the granular core portion before formation of the coating layer portion is less than the lower limit, the materials that form the coating layer portion do not adhere to the periphery of the granular core portion. That is, when the moisture content of the granular core portion is less than 20 wt %, the coating layer portion, which has a specific thickness necessary for demonstrating a specific action, is not formed, and as a result, no multi-layer water absorbing material is formed, separation of the coating layer portion occurs, no aggregate is created after use, and the appearance is poor. Therefore, such a moisture content is not preferable.

On the other hand, a moisture content of the granular core portion exceeding 41 wt % is not preferable because, for example, the drying step takes a long period of time. Accordingly, in the case of performing the aforementioned extruding granulation, it is preferable to adjust the moisture content of the granular core portion so as to be 20 wt % to 41 wt % (more preferably 20 wt % to 25 wt %).

(2) Excretion Test Indicator Adsorption Step (S2)

This step is for preparing an excretion test material.

This step is for allowing a test indicator-containing ink composition produced by dissolving the test indicator in a solvent to be adsorbed on a porous adsorbent.

In this step, a test indicator-containing ink composition produced by a known method is added dropwise little by little to, and is blended with, a porous adsorbent that has been processed into fine powder in order to allow the test indicator to be adsorbed on the porous adsorbent to prepare an excretion test material.

The proportions of the test indicator and the porous adsorbent are determined according to the adsorbance of the porous adsorbent. However, when the amount of the porous adsorbent added exceeds a specific amount, particles of the porous adsorbent are exposed from the surface layer of the coating layer portion, and thus such exposed portions project from the surface layer in the form of protrusions. Then, grains of the water absorbing material are brought into contact with each other during packaging and transportation, and thus the projecting portions separate from the base portions, creating a condition where, for example, a damaged surface layer portion is present. Therefore, such an amount is not preferable.

It is necessary that the test indicator is added in an amount more than 0.1 wt % and not more than 1.0 wt % relative to the total amount of the coating layer portion, and when the test indicator is fixed to the ink composition, the amounts of the solvent and other components are adjusted such that the test indicator is within the aforementioned range.

Meanwhile, since every porous adsorbent has its own largest adsorbance, the minimum required amount of the porous adsorbent is determined so as to allow a necessary test indicator to be adsorbed thereon, and therefore the test indicator-containing ink composition is adsorbed on the porous adsorbent of the amount thus determined.

(3) Coating Material Production Step (S3)

This step is for producing a coating material constituting the coating portion.

This step is for producing a coating material by adding the excretion test material prepared in the excretion test indicator adsorption step to a substrate composed of specific materials and mixing them in specific proportions so as to attain the desired amount of the test indicator.

Note that addition of desired materials such as a penetrating agent and a swelling agent other than the coating material and the excretion test material to the coating layer portion is carried out in this step.

(4) Coating Step (S4)

This step is for forming the coating layer portion by coating the periphery of the granular core portion with the coating material. In this step, the coating material is sprayed around the granular core portion using a coating device or the like to form the coating layer portion. In this manner, an operation for producing a multi-layer water absorbing material is performed.

(5) Classification Step (S5)

This step is for classifying particles of the water absorbing material so as to have a specific size.

In this step, the water absorbing material produced in the previous step is sifted with a sieve having a specific mesh size to separate products that do not have a specific size. In this manner, an operation for obtaining only the products that have a specific size is performed.

(6) Drying Step (S6)

This step is for drying the obtained water absorbing material having a specific size using a dryer.

In the case where the moisture content of the granular core portion is high during storage of the water absorbing material, the moisture of the granular core portion leaches out for an extended period of time, thus resulting in quality deterioration, and such a moisture content is thus not preferable. Therefore, drying is carried out such that the moisture content of the granular core portion is within the range between 3% or greater and 10% or less so as to be able to prevent quality deterioration during storage.

[Functional Effects]

Regarding the water absorbing material of the present invention, the test indicator is not directly added to the components of the coating layer portion, but the test indicator is first dissolved in a solvent and formed into a test indicator containing ink composition, and then adsorbed on a porous adsorbent. Since the test indicator is evenly adsorbed in a large number of pores present in the porous adsorbent, it is possible to uniformly retain the test indicator in an amount that enables a color change or a lightness change to be clearly identified without carrying out a special treatment.

Since the test indicator is blended in the coating layer portion, the coating layer portion promptly undergoes a color change as the test indicator is brought into contact, and it is thereby possible to readily determine a test result in a short period of time. Moreover, with the water absorbing material of the present invention, the amount of the test indicator added is greater than 0.1 wt % relative to the total amount of the coating layer portion, thus allowing the test indicator to develop color with specific lightness and chroma before use, and thus making it possible to retain an agreeable appearance. Therefore, even in the case where the water absorbing material of the present invention is used in combination with an inexpensive water absorbing material that is of a type that does not contain a test indicator or a coloring agent, a specific test can be carried out, and thus the water absorbing material of the present invention can be an economically advantageous water absorbing material.

So far, one preferable embodiment has been described, but the present invention is not limited to that embodiment, and design modifications can be suitably performed without departing from the scope of the present invention. In the present embodiment, a description has been provided using as an example a water absorbing material for pets for treating excretion. Needless to say, however, the water absorbing material may be applied to humans and other animals.

In addition, a description has been provided using a urinary pH value detection indicator as an example of the test indicator, but the test indicator is not limited thereto, and urinary glucose detection indicators, urinary protein detection indicators, urinary occult blood detection indicators, urinary urobilinogen detection indicators, or like various indicators are usable.

Moreover, in the description provided above, the excretion test indicator adsorption step has been described as being performed after the granulation step, but these steps may be performed chronologically in parallel, and in addition to the aforementioned steps, other steps may be suitably added.

If a plurality of different types of test indicators are dissolved in a solvent and adsorbed on a porous adsorbent, and the mixture is added to a coating layer portion, multiple test results can be determined at once.

EXAMPLES

To investigate the performance of the water absorbing material of the present invention, samples were prepared according to the production method described below, and a color production test was carried out.

<Components>

Each sample used in the following test was produced according to the production method of the present invention, and was a multi-layer water absorbing material composed of a granular core portion and a coating layer portion. The weight ratio between the materials constituting the granular core portion and the coating layer portion was 83 wt % to 17 wt %, and a 1000 g sample was produced.

(1) Granular Core Portion

Ingredients were virgin pulp (50 wt %, a water content of 8.0%), pulp sludge (49 wt %, a water content of 57.0%), and cornstarch (1 wt %, a water content of 9.0%).

(2) Coating Layer Portion

The coating layer portion was prepared by mixing a substrate (a mixture of virgin pulp and carboxymethylcellulose) (provided that their mixing ratio in wt % was the same) and an excretion test material.

The excretion test material was composed of a test indicator-containing ink composition and a porous adsorbent.

As the test indicator-containing ink composition, a composition prepared by dissolving bromothymol blue (a test indicator) (manufactured by Advantec Toyo Co., Ltd.) and a cellulose-based resin in an organic solvent (industrial ethyl alcohol and methyl alcohol) was used (both manufactured by Toyo Ink MFG. Co., Ltd.), and samples were produced with varying amounts of the test indicator added.

Fine powder of silica gel (A type) (manufactured by Hymo Co., Ltd.) was used as the porous adsorbent.

<Samples>

The coating layer portion contained the substrate in 93 wt % and the excretion testing material in 7 wt % relative to the total weight. The amounts of the test indicator blended relative to the total amount of the coating layer portion were 0.09 wt %, 0.10 wt %, 0.11 wt %, 0.15 wt %, 0.20 wt %, 0.30 wt %, 0.40 wt %, 0.50 wt %, 0.60 wt %, 0.70 wt %, 0.80 wt %, 0.90 wt %, 1.00 wt %, and 1.10 wt %, thus giving a total of 14 samples having different blending proportions.

<Observation Results>

The extent of color development of the coating layer portion of each sample was visually inspected before use and after adding dropwise a suitable amount of physiological saline (having a sodium chloride concentration of 0.9 wt %) such that the pH was 6.8 (corresponding to after-use), and the lightness according to the Munsell color system was measured (Table 1).

(1) Samples 1 and 2 that had an amount of the test indicator added relative to the total weight of the coating layer portion of 0.09 wt % and 0.10 wt %, respectively, demonstrated inappropriate results in that the color development of the coating layer portions were not visible before use.

TABLE 1

| | Sample No. | | | | | | |
|---|---|---|---|---|---|---|---|
| | 1 | 2 | 3 | 4 | 5 | 6 | 7 |
| Amount of test indicator blended (wt %) | 0.09 | 0.10 | 0.11 | 0.15 | 0.20 | 0.30 | 0.40 |
| Lightness before dropwise addition of mock urine | Color did not develop | Color did not develop | 8 | 7 | 6 | 6 | 5 |
| Lightness after dropwise addition of mock urine | — | — | 6 | 5 | 4 | 4 | 3 |

| | Sample No. | | | | | | |
|---|---|---|---|---|---|---|---|
| | 8 | 9 | 10 | 11 | 12 | 13 | 14 |
| Amount of test indicator blended (wt %) | 0.50 | 0.60 | 0.70 | 0.80 | 0.90 | 1.00 | 1.10 |
| Lightness before dropwise addition of mock urine | 5 | 4 | 3 | 3 | 3 | 2 | 1 |
| Lightness after dropwise addition of mock urine | 3 | 2 | 2 | 2 | 2 | 1 | 1 |

(2) In contrast, samples 3 and 13 that had an amount of the test indicator added relative to the total weight of the coating layer portion of 0.11 wt % to 1.0 wt % developed a specified color of green before use. Then, when the same mock urine as stated above was added dropwise (corresponding to after-use), each demonstrated enhanced lightness and enabled the after-use conditions to be confirmed, thus giving favorable results. In particular, it was easy to visually recognize the lightness change before and after use of samples 4 to 8 that had an amount of the test indicator added of 0.15 wt % to 0.50 wt %.

Note that it was confirmed that when a suitable amount of physiological saline (having a sodium chloride concentration of 0.9 wt %) was added to each sample such that the pH was 8.0, the color changed to blue that had the same lightness.

(3) Regarding sample 14 that had an amount of the test indicator added of 1.10 wt % relative to the total weight of the coating layer portion, green color was developed before and after use, but its lightness did not change, thus demonstrating inappropriate results in that the after-use conditions cannot be confirmed.

According to the results of the color development tests presented above, it is clear that the amount of the test indicator added relative to the total weight of the coating layer portion is suitably within the range between greater than 0.1 wt % and equal to or less than 1.0 wt % (in particular, preferably 0.15 wt % to 0.50 wt %).

REFERENCE SIGNS LIST

S1 Granulation step
S2 Excretion test indicator adsorption step
S3 Coating material production step
S4 Coating step
S5 Classification step
S6 Drying step

The invention claimed is:

1. A water absorbing material comprising:
a granular core portion and a coating layer portion coating the granular core portion,
the coating layer portion being composed of 90 wt % to 96 wt % of a substrate and 10 wt % to 4 wt % of an excretion test material, the substrate consisting essentially of a mixture of virgin pulp and carboxymethylcellulose,
the excretion test material containing a porous adsorbent having an adsorbance of 20 wt % or greater and including micropores, and an excretion test indicator adsorbed on the micropores of the porous adsorbent,
the excretion test indicator being added in an amount more than 0.1 wt % and not more than 1.0 wt % relative to a total amount of the coating layer portion, and being not present in the water absorbing material other than in the porous adsorbent.

2. The water absorbing material according to claim 1, wherein the excretion test indicator is fixed to an ink composition.

3. The water absorbing material according to claim 1, wherein the excretion test indicator is adsorbed on the micropores of the porous adsorbent prior to mixing the excretion test material with the substrate.

4. The water absorbing material according to claim 1, wherein the excretion test indicator develops color before and after use of the water absorbing material, and a lightness of the color changes before use and after use of the water absorbing material.

5. The water absorbing material according to claim 1, wherein the porous adsorbent is type B silica gel.

6. The water absorbing material according to claim 1, wherein a plurality of different types of the excretion test indicators are adsorbed on the micropores of the porous adsorbent.

* * * * *